United States Patent [19]

Yoshida et al.

[11] Patent Number: 5,107,214

[45] Date of Patent: Apr. 21, 1992

[54] HOT FLAW DETECTOR WITH ANNULAR INJECTION PORT FOR INJECTING COOLING LIQUID

[75] Inventors: Mitsuo Yoshida; Shigeyuki Nitta; Kazuyoshi Miyazawa, all of Muroran; Katsumi Taguchi; Masaki Fujiwara, both of Tokyo, all of Japan

[73] Assignees: Nippon Steel Corporation; Eddio Corporation, both of Tokyo, Japan

[21] Appl. No.: 602,242

[22] PCT Filed: Mar. 7, 1990

[86] PCT No.: PCT/JP90/00296

§ 371 Date: Nov. 7, 1990

§ 102(e) Date: Nov. 7, 1990

[87] PCT Pub. No.: WO90/10864

PCT Pub. Date: Sep. 20, 1990

[30] Foreign Application Priority Data

Mar. 9, 1989 [JP] Japan .................... 1-57238

[51] Int. Cl.[5] .................... G01N 27/90; G01R 33/12
[52] U.S. Cl. .................... 324/224; 324/226; 324/238
[58] Field of Search .............. 324/224, 225, 226, 238, 324/240, 262

[56] References Cited

U.S. PATENT DOCUMENTS

| | | | |
|---|---|---|---|
| 3,694,735 | 9/1972 | Mester | 324/226 X |
| 4,123,708 | 10/1978 | Vild et al. | 324/224 |
| 4,461,995 | 7/1984 | Harris | 324/224 |
| 4,789,828 | 12/1988 | Tornblom | 324/224 |
| 4,810,988 | 3/1989 | Schenk, Jr. et al. | 324/224 X |

FOREIGN PATENT DOCUMENTS

| | | | |
|---|---|---|---|
| 45-26143 | 10/1970 | Japan . | |
| 0012790 | 1/1979 | Japan | 324/224 |
| 54-26072 | 8/1979 | Japan . | |
| 0097486 | 8/1979 | Japan | 324/224 |
| 58-83254 | 10/1982 | Japan . | |
| 60-18938 | 5/1985 | Japan . | |
| 61-747 | 1/1986 | Japan . | |

*Primary Examiner*—Gerard R. Strecker
*Attorney, Agent, or Firm*—Fleit, Jacobson, Cohn, Price, Holman & Stern

[57] ABSTRACT

A hot flaw detector is equipped with a sensor holding member that has a circular opening through which the material to be inspected will pass and that holds a flaw detecting sensor. Provision is made of an annular cooling liquid injection port that is open at an end of the sensor holding member adjacent to the inner peripheral wall of the circular opening, and provision is further made of an annular cooling liquid introduction port that is open at the other end of the sensor holding member adjacent to the inner peripheral wall of the circular opening. The cooling liquid is injected from the annular cooling liquid injection port, and forms a liquid film along the inner peripheral wall of the circular opening, and is recovered through the annular cooling liquid introduction port. The inner peripheral wall of the sensor holding member is effectively cooled by the liquid film which drips little onto the material to be inspected.

4 Claims, 3 Drawing Sheets

HOT FLAW DETECTOR WITH ANNULAR INJECTION PORT FOR INJECTING COOLING LIQUID

TECHNICAL FIELD

The present invention relates to a through-type eddy current hot state flaw detector for detecting flaws in ferromagnetic metals such as wires, steel bars, steel pipes, etc., and in non-magnetic metal materials in the step of hot rolling. More specifically, the invention relates to a hot flaw detector which requires no sleeve for shielding the heat.

BACKGROUND ART

Electromagnetic induction (eddy-current) flaw detecting method has heretofore been widely used for non-destructive inspection of metal wires and bars that are hot rolled to meet initial prerequisites such as high-speed and non-contact operation. A variety of heat shielding and cooling constructions have been devised for the sensor unit used for the flaw detection since it always confronts the materials of high temperatures that are to be inspected.

In order to protect the sensor unit from high temperatures radiated from the materials to be inspected, heat-resistant coils for eddy-current flaw detection employing a heat-shielding thin-wall sleeve have long been put into practical use as disclosed in Japanese Utility Model Application Publication No. 45-26143, U.S. Pat. No. 3,694,735, Japanese Application Public Disclosure No. 58-83254, and U.S. Pat. No. 4,461,995. In the heat-resistant coils for eddy current flaw detection, the thin-wall sleeve for shielding is made up of a thin-wall pipe composed of an austenite-type stainless steel or titanium resulting, however, in the development of eddy-current loss since it is an electrically conductive material. That is, the magnetic lines of force of the flaw detecting exciting coils or of the detecting coils surrounding the outer circumference of the thin-wall pipe are attenuated by the thin-wall pipe as they reciprocally travel through the hot material to be tested running inside the thin-wall pipe. Attempts were made to replace the thin-wall pipe by a non-metallic pipe such as a ceramic cylinder of alumina or the like without, however, any success of putting it into practice in regard to mechanical resistance and thermal shock resistance.

In order to solve such problems, it was devised to form a single or a plurality of elongated grooves in the heat-shielding sleeve which is made up of a thin metal pipe as disclosed in Japanese Utility Model Application Publication No. 54-26072 and Japanese Patent Application Publication No. 60-18938. With the structure disclosed in Japanese Utility Model Application Publication No. 54-26072, however, the cooling water flows out through the elongated grooves. With the structure disclosed in Japanese Patent Application Publication No. 60-18938, on the other hand, the leakage of water can be prevented by sealing the elongated grooves with a filler material or a junction material. However, since the heat-shielding sleeve and the filler material or the junction material have different coefficients of thermal expansion, the filler material or the junction material is split off causing, after all, the water to leak. There have further been proposed hot eddy-current flaw detecting coils in which the cooling water is positively injected from the heat-shielding member of the hot flaw detecting coil to locally cool the outer surface of the pipe to be inspected after the flaw detecting coil is cooled as disclosed in U.S. Pat. Nos. 4,024,470 and 4,123,708. With the eddy-current flaw detection being carried out while permitting the water to be leaked as done in Japanese Utility Model Application Publication No. 54-26072 and Japanese Patent Application Publication No. 60-18938 and in U.S. Pat. Nos. 4,024,470 and 4,123,708, however, there arises a problem in that the outer surface of the material to be tested is locally cooled.

Therefore, there have been proposed the structures for effecting the cooling without using heat-shielding electrically conductive sleeve which deteriorates the sensitivity of the flaw sensor and without permitting the cooling water to come in contact with the outer surface of the material to be inspected, as disclosed in Japanese Patent Application Public Disclosure No. 61-747. According to the hot flaw detector without sleeve disclosed in Japanese Patent Application Public Disclosure No. 61-747 which uses no heat-shielding metals, the flaw detecting sensitivity in improved by forming a water film along the inner peripheral wall of a non-metallic high molecular coil bobbin such as of nylon or Teflon by using water emitted from the outlet of the coil bobbin, thereby to shield the heat with the water film and to cool. That is, with the structure disclosed in this Japanese Patent Application Public Disclosure No. 61-747 which uses no stainless steel cylinder, the alternating magnetic field for flaw detection is not interrupted by the stainless steel cylinder that was so far used to shield the heat, and the cooling is effected efficiently, too.

With the structure of the hot flaw detector without the sleeve disclosed in the aforementioned Japanese Patent Application Public Disclosure No. 61-747, however, special experience and skill are needed to form a plurality of outlet ports in the coil bobbin maintaining a distance among the ports, an opening width in the axial direction and skews in the water outlet paths with predetermined precision, such that the water emitted from the outlet ports forms a water film along the inner wall and periphery of the cylindrical coil bobbin, spirally whirls toward the exit side, and is drained. If the machining is not well done, ripples develop on the water film whirling along the inner wall of the flaw detecting coil, and the cooling is not effected uniformly.

At the present time in Japan, the hot rolling operation is so carried out as to increase the productivity while giving attention to effecting the low-temperature rolling at near a Curie point and reducing the surface oxidation (scale) of the material to be inspected as a result of low-temperature rolling from the standpoint of saving energy and saving resources. FIG. 5 of the accompanying drawings is a graph showing the working temperatures of carbon steels quoted from the "Handbook of Steels III", from which it will be understood that the hot working region at present is extending up to a region designated by reference symbol $A_2$. Water-tightening is reinforced so that the roll cooling water will not come in contact with the rolled material in order to save energy, i.e., to prevent the loss of heat. The temperature for heating the material is lowered by the amount of temperature drop that could be prevented by the above countermeasure, contributing to decreasing the fuel cost. Local cooling with water that is positively effected during the hot rolling hinders the operation for saving energy and further impairs the object of gradual cooling after the completion of rolling, and further causes the surface to be hardened and particle sizes to become nonuniform after the smelting. From such a point of view, the structure of the hot flaw detector without sleeve disclosed in the aforementioned Japanese Patent Application Public Disclosure No. 61-747 is not perfect in regard to draining water after the water film is formed to effect the cooling. That is, the water that has whirled along the inner wall of the flaw detecting coil falls due to the force of gravity and comes in contact with the material to be inspected and cools it.

DISCLOSURE OF INVENTION

The object of the present invention is to provide a hot flaw detector which is capable of eliminating the above-mentioned problems inherent in the prior art.

The present invention is concerned with a hot flaw detector equipped with a sensor holding member that has a circular opening through which the material to be inspected will pass and that holds a flaw detecting sensor, which further comprises an annular cooling liquid injection port that is open at an end of said sensor holding member adjacent to the inner peripheral wall of said circular opening, and an annular cooling liquid introduction port that is open at the other end of said sensor holding member adjacent to the inner peripheral wall of said circular opening, wherein the cooling liquid injected from said annular cooling liquid injection port forms a liquid film along the inner peripheral wall of said circular opening and is recovered through said annular cooling liquid introduction port.

An embodiment of the present invention will now be described in further detail in conjunction with FIGS. 1 to 4 of the accompanying drawings.

BEST MODE FOR CARRYING OUT THE INVENTION

Figure 1:
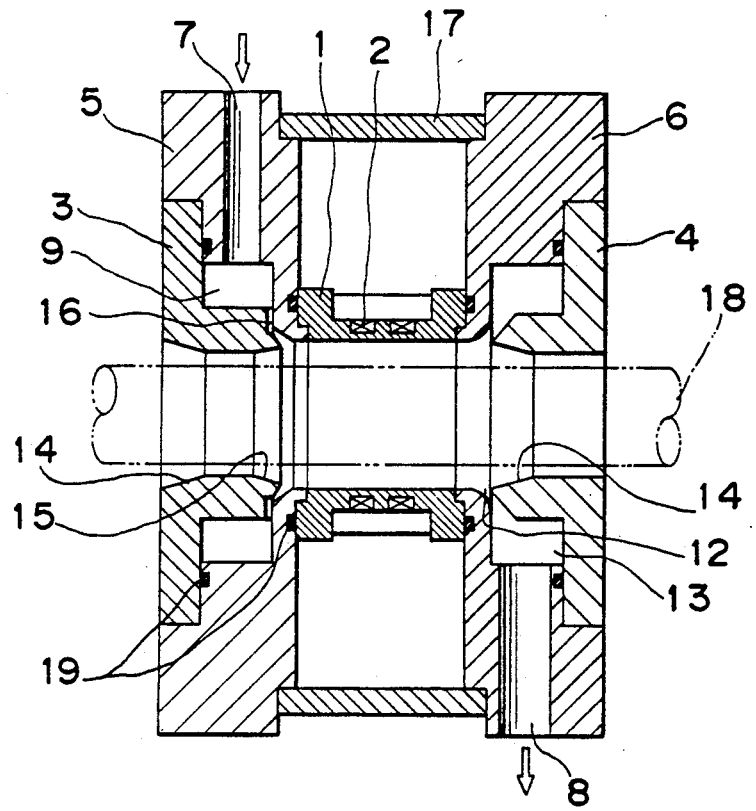
FIG. 1 is a schematic section view of a hot flaw detector according to an embodiment of the present invention.

Referring to FIG. 1, the hot flaw detector according to an embodiment of the present invention is equipped with a coil bobbin 1 on which a flaw detecting coil 2 is wound, an input guide flange 3 and an output guide flange 4 that guide the insertion of the material to be inspected in the coil bobbin 1, an input side plate 5 and an output side plate 6 for firmly mounting the coil bobbin 1, the input guide flange 3 and the output guide flange 4, and a frame 17 which couples the input side plate 5 and the output side plate 6 together as a unitary structure.

Figure 3:
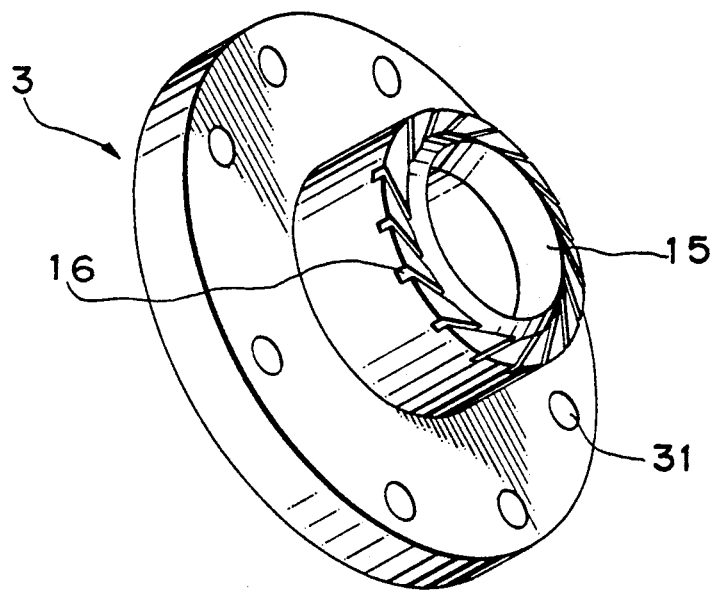
FIG. 3 is a perspective view showing the input guide flange only.
Figure 4:
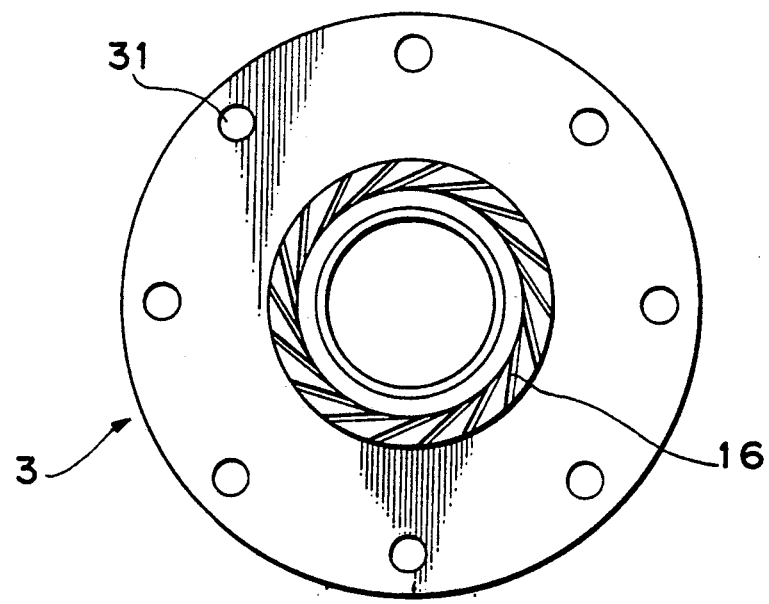
FIG. 4 is a diagram of when the input guide flange of FIG. 3 is viewed from the right side.
Figure 5:
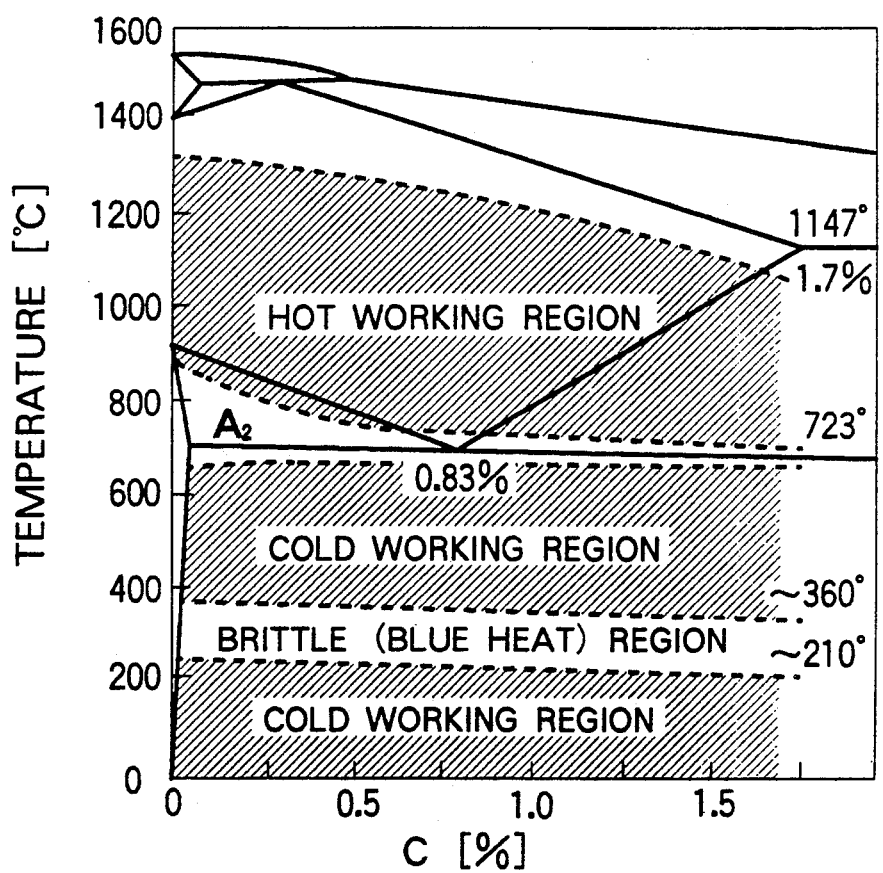
FIG. 5 is a graph showing the working temperatures for the carbon steels.

FIG. 3 is a perspective view showing the input guide flange 3 only, and FIG. 4 is a diagram of when the input guide flange 3 of FIG. 3 is viewed from the right side. As best shown in FIGS. 3 and 4, the input guide flange 3 has a plurality of water paths 16 that are radially formed. Reference numeral 31 denotes bolt holes in which the bolts are inserted to fasten the input guide flange 3 to the input side plate 5.

Figure 2:
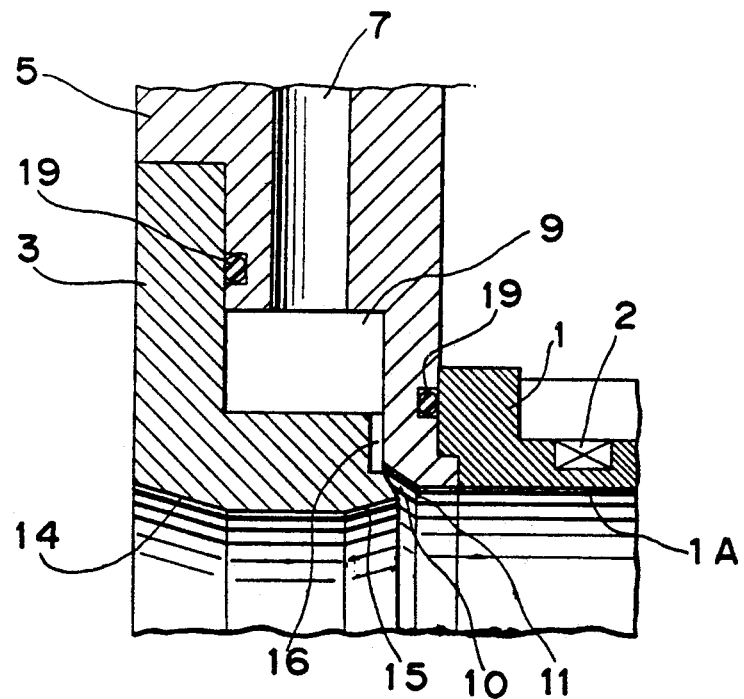
FIG. 2 is a diagram showing on an enlarged scale a portion of FIG. 1 to illustrate in detail a relationship between the input guide flange and the input side plate in the hot flaw detector of FIG. 1.

FIG. 2 is a diagram showing on an enlarged scale a portion of FIG. 1 to illustrate in detail a relationship between the input guide flange 3 and the input side plate 5. The constitution and operation of the hot flaw detector of the embodiment will now be described in detail in conjunction with FIGS. 1 and 2.

A cooling water feed port 7 is formed in the input side plate 5, and the cooling water enters through the feed port 7 and enters into a cooling water tank 9 that is provided between the input side plate 5 and the input guide flange 3. The cooling water filled in the cooling water tank 9 flows through the radial water paths 16 formed in the inside guide flange 3 and is emitted along the inner peripheral surface 1A of the coil bobbin 1 from injection ports 10. The cooling water emitted from the injection ports 10 formed between the input guide flange 3 and the input side plate 5 whirls in a direction in which it is injected along the inner peripheral surface 1A of the coil bobbin 1 from spray-turn starting portions designated at 11 in FIG. 2 thereby to form a spiral water film. In order to effectively form the cooling water film over the whole inner peripheral surface 1A of the coil bobbin 1 to meet the inner diameter of the flaw detecting coil 2, it is necessary to suitably select the number of radial water paths 16 formed in the input guide flange 3, the width of the water paths, distance among the water paths, angle of the water paths, and the like.

In order to easily recover and drain the cooling water that has formed the water film along the inner peripheral surface 1A of the coil bobbin 1, a water drain path 12 and a water drain tank 13 are concentrically formed between the output side plate 6 and the output guide flange 4, and a water drain port 8 is formed in the output side plate 6. As described above, the cooling water film formed along the inner peripheral surface 1A of the coil bobbin 1 is taken into the water drain tank 13 through the water drain path 12, and is drained through a water drain port 8.

The input guide flange 3 and the output guide flange 4 have inner diameters that are slightly smaller than the inner diameter of the coil bobbin 1, so that the outer surface of the material 18 to be inspected that passes through will not come in contact with the inner peripheral surface 1A of the coil bobbin 1. Further, the input guide flange 3 and the output guide flange 4 are tapered as designated at 14 and 15, so that the material 18 to be inspected is allowed to pass through easily.

With the device being constructed as described above, the cooling water introduced through the cooling water feed port 7 is sent to the water paths 16 through the cooling water tank 9. The water paths 16 are radially formed maintaining such an angle that the cooling water is emitted in the tangential direction of the inner peripheral surface 1A of the coil bobbin 1. Therefore, the cooling water emitted from the injection ports 10 forms a spiral water film along the inner peripheral surface 1A of the coil bobbin 1 starting from the spray-turn start portions 11. The cooling water that formed the water film and that performed the cooling enters into water drain paths 12, recovered in the water drain tank 13, and is drained through the water drain port 8.

Reference numeral 19 denotes an O-ring that is provided between the input guide flange 3 and the input side plate 5 to maintain water-tightness, an O-ring that is provided between the output guide flange 4 and the output side plate 6 to maintain water-tightness, an O-ring that is provided between the input side plate 5 and the coil bobbin 1 to maintain water-tightness, and an 0-ring that is provided between the output side plate 6 and the coil bobbin 1 to maintain water-tightness.

According to the hot flaw detector of the present invention constituted as described above, the inner peripheral surface of the sensor holding member that holds the flaw detecting sensor such as eddy-current flaw detecting coil or the like, is efficiently cooled by the liquid film formed by the cooling liquid such as water injected from the injection ports provided at an end of the sensor holding member, and the liquid film after it has effected the cooling is recovered through the cooling liquid introduction ports provided at the other end of the sensor holding member. Therefore, the cooling is effected very efficiently, and the cooling liquid is recovered without being sprayed in droplets onto the material to be inspected, contributing to saving energy. Further, when the eddy-current flaw detecting coil is used as the flaw detecting sensor, there is no need of using a metallic sleeve that develops eddy current loss and deteriorates the detection sensitivity. Therefore, the detection sensitivity can be improved and the inner diameter of the eddy-current flaw detecting coil can be decreased correspondingly.

What is claimed is:

1. A hot flaw detector comprising:
    a flaw detecting sensor;
    structural means for providing a circular opening through which the material to be inspected will pass and which defines an inner peripheral wall within the opening extending between longitudinal ends of the opening and for holding the flaw detecting sensor;
    annular injection port means for injecting cooling liquid at a first end of said circular opening and adjacent to the inner peripheral wall of said circular opening, for swirling cooling liquid about the inner peripheral wall and for directing the liquid from the first end toward a second end of said circular opening; and
    annular drain path means for recovering said cooling liquid at the second end of said circular opening and adjacent to the inner peripheral wall of said circular opening, and
    wherein the cooling liquid injected from said annular injection port means forms a liquid film along the inner peripheral wall of said circular opening.

2. A hot flaw detector according to claim 1, wherein said annular injection port means includes a plurality of grooves that are tangentially directed relative to the center of said circular opening for forming a liquid stream that whirls in a predetermined direction along the inner peripheral wall of said circular opening for providing said liquid film.

3. A hot flaw detector according to claim 1, wherein said flaw detecting sensor includes an eddy-current flaw detecting coil, and said structural means includes a coil bobbin about which the flaw detecting coil is wound.

4. A hot flaw detector according to claim 1, wherein said cooling liquid is water.

* * * * *